United States Patent [19]

Heller

[11] Patent Number: 5,667,514

[45] Date of Patent: Sep. 16, 1997

[54] DEVICE AND METHOD FOR INSERTING A FLEXIBLE ELEMENT INTO SOFT TISSUE

[75] Inventor: James Heller, Englewood, Colo.

[73] Assignee: Cochlear Ltd., Lane Cove, Australia

[21] Appl. No.: 534,510

[22] Filed: Dec. 4, 1995

[51] Int. Cl.$^6$ ........................................................ A61F 11/00
[52] U.S. Cl. ............................ 606/108; 604/160; 604/161; 604/164
[58] Field of Search ............................ 606/124, 108; 604/160, 161, 165, 109, 158, 164, 166, 171

[56] References Cited

U.S. PATENT DOCUMENTS 4,166,469  9/1979  Littleford ........................ 128/784
4,243,050  1/1981  Littleford ........................ 128/784
4,345,606  8/1982  Littleford ........................ 128/784

*Primary Examiner*—Robert A. Hafer
*Assistant Examiner*—Justine R. Yu
*Attorney, Agent, or Firm*—Gottlieb, Rackman & Reisman

[57] ABSTRACT

An inserting device is provided for inserting an elongated thin flexible surgical member, such as an electrode, and the like, into body tissues. The device includes a pair of tubular portions with longitudinal slits. The two members define a lumen for accepting the surgical member after the device is introduced into the tissues. Thereafter, the members are positioned so that the slits are aligned to provide an opening which allows the inserting device to be withdrawn without interfering with the inserted surgical instrument. An enforcing element, such as an obturator, may be inserted into the lumen while the inserting device is introduced into the tissues.

16 Claims, 4 Drawing Sheets

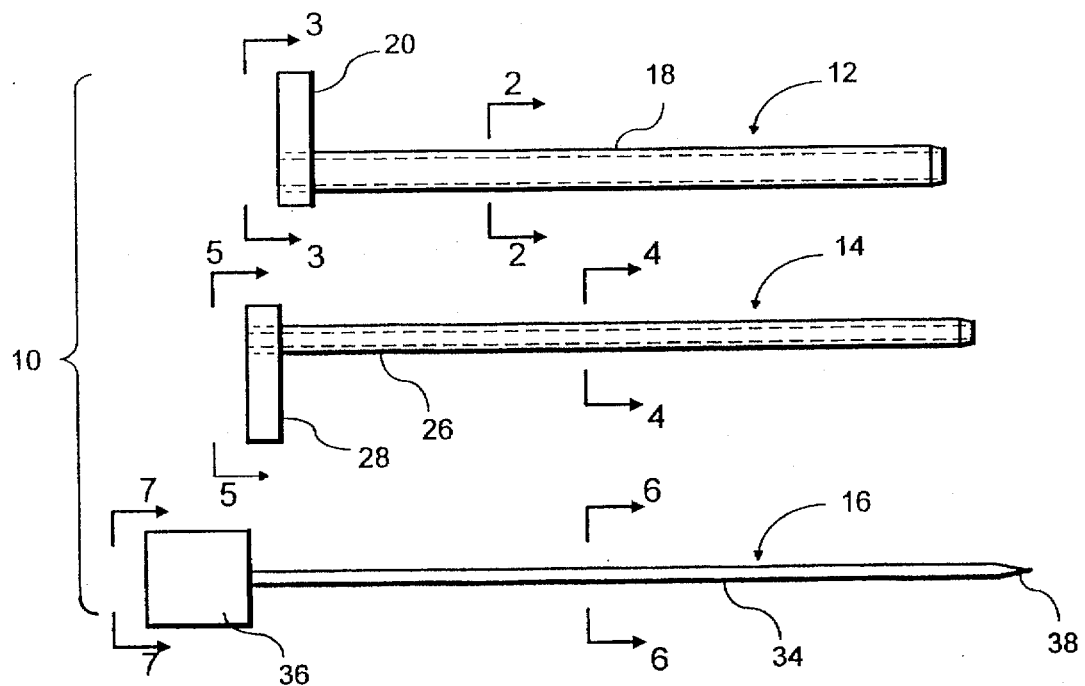
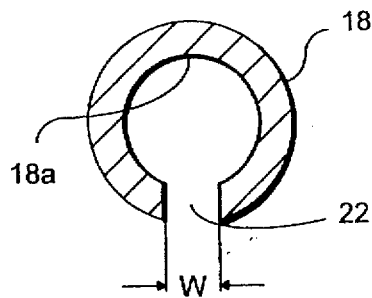
FIG. 2
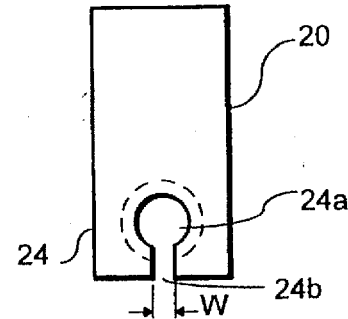
FIG. 3
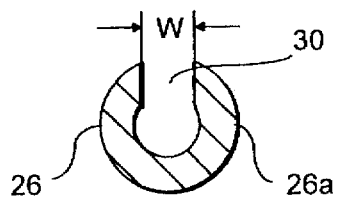
FIG. 4
FIG. 6
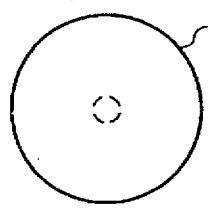
FIG. 7
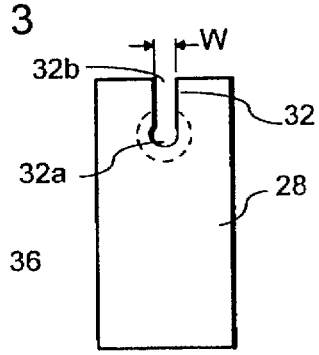
FIG. 5

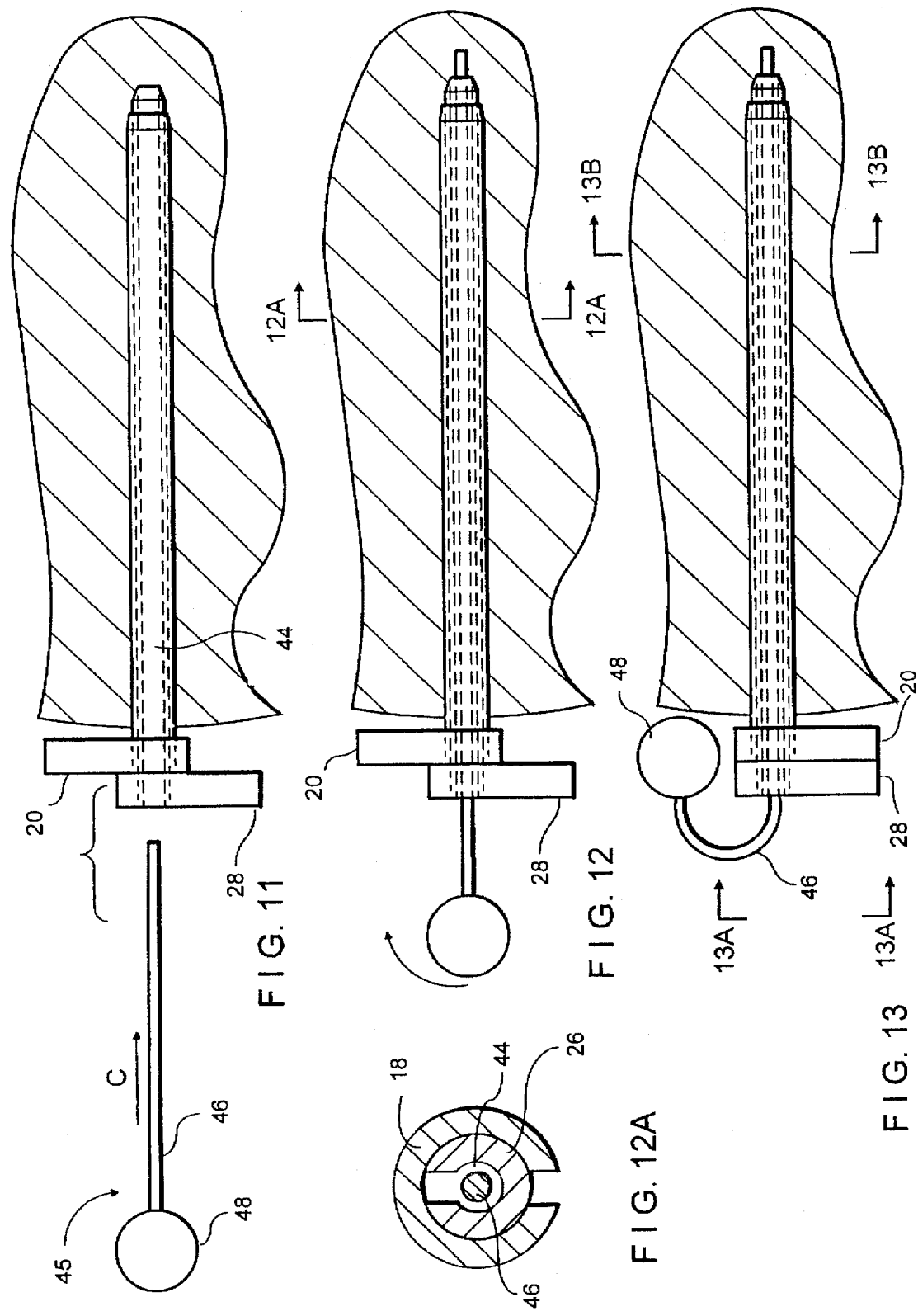

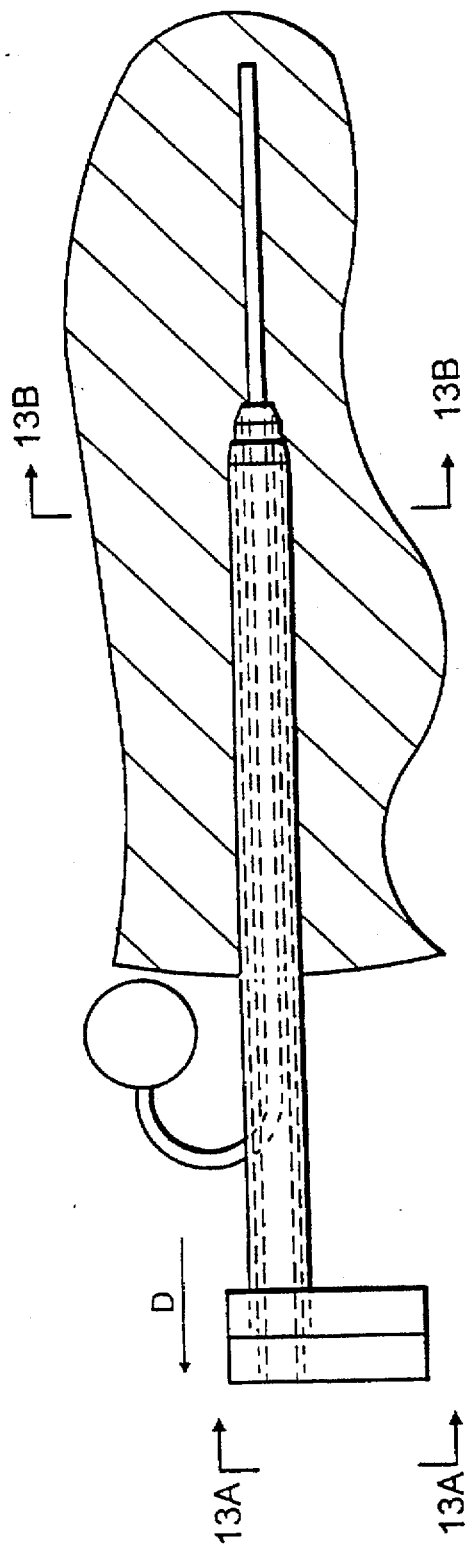
FIG. 13A
FIG. 13B
FIG. 14

DEVICE AND METHOD FOR INSERTING A FLEXIBLE ELEMENT INTO SOFT TISSUE

BACKGROUND OF THE INVENTION

1. Field of Invention

This invention pertains to a surgical device for inserting an elongated flexible element having an enlarged proximal end, such an electrode, a probe, a catheter and so on, into a body cavity whereby the element is precisely and easily positioned within the body. The device and method includes the use of a split sleeve which envelopes the element, and which after insertion, can be withdrawn easily and removed from the elongated element without interference from the element proximal end.

2. Description of the Prior Art

Many surgical procedures entail the insertion of an elongated element into a body cavity, which element may be left temporarily, semi-permanently or permanently in the body. For example, one type of such an elongated element is a catheter inserted into a body tissue or organ for the purpose of fluid drainage, fluid infusion, and so on. This type of catheter is provided with an enlarged proximal end, such as Luer connector used for coupling the catheter to a corresponding drainage or infusion device. Another type of flexible element is a probe used for localized tissue treatment using electrical stimulation, heating cooling, radiation, cutting or evacuation. A third type of flexible element is an electrode used for sensing, monitoring and diagnostic functions.

Typically all these elements are place accurately without open surgery by using ultrasonic, endoscopic, fluoroscopic, or X-ray imaging, as well as using stereotactic methods. However a problem with all the elements described above is that because of their very flexibility, it is difficult to feed them and to maneuver them during insertion because the element has insufficient rigidity to pierce or penetrate the various body tissues and/or orifices. This problem has been solved in the past by adding a member which increases the rigidity of the element. However this approach is only possible for elongated elements having a lumen which can accept the rigidifying member. Probes without such a lumen need other stiffening means, such as for example a tube which splits in half along its longitudinal axis after insertion as described U.S. Pat. Nos. 4,166,469;, 4,243,050; 4,345, 606.

These latest devices include a tube which receives the flexible element for insertion and later, after the insertion is completed, peels away by separation along a longitudinal frangible zone or line to permit the reinforcing member to be withdrawn past the proximal enlarged end of the elongated element. However this approach is not satisfactory because the required structure can be accomplished with only very thin materials for the reinforcing member whereby the reinforcing member itself is not rigid enough, and also the peeling away can move the flexible element. This problem is especially acute for extra thin elements such as required of example in special applications such as stereotactic brain surgery.

Other systems have been proposed which provide the insertion of the reinforcing element in parallel to the elongated element with locking mechanism such as a hook-and-loop arrangement being provided at the tip or distal end. However this approach is also unsatisfactory because a method or technique must be provided for opening the locking mechanism after the insertion. Moreover, the locking mechanism increases the physical complexity of the elongated element, and its cost.

OBJECTIVES AND SUMMARY OF THE INVENTION

In view of the above-mentioned disadvantages of the prior art, an objective of the present invention is to provide a device for inserting an elongated element into a body cavity, which device is easy to use with substantially any kind of element without interference with the element's proximal end.

A further objective is to provide a device which is relatively inexpensive so that it can be made disposable.

Yet another objective is to provide an insertion device which is easy to manufacture and has relatively few surfaces so that it can be sterilized effectively.

Yet another objective is to provide an insertion device which allows very accurate positioning of the flexible element.

Other objectives and advantages shall become apparent from the following description. Briefly, a device for inserting an elongated therapeutic element into a body cavity consists of two telescoping members constructed and arranged to form a tube for insertion into the body. Preferably the members are made of a relatively stiff material to form a rigid tube so that it can pierce body tissues, if necessary. Preferably, the tube defines a lumen fox receiving the elongated element. The two members are movable between a first configuration for forming said tube and a second configuration in which a longitudinal slot is formed to allow the members to be separated from the elongated element. The two members are provided with respective handles which allow the members to be manipulated from one configuration to the other by the user.

The two members, with optionally a reinforcing element, are assembled to form the insertion device which is then introduced into the body tissue. The reinforcing element (if any) is then withdrawn from the two members leaving a lumen. The elongated element is introduced into the lumen. The two members are repositioned into the second configuration and withdrawn, leaving the elongated element in place.

BRIEF DESCRIPTION OF THE DRAWINGS

FIG. 1 shows the members that make up the insertion device constructed in accordance with this invention;

FIG. 2 is a cross sectional section taken along line 2—2 in FIG. 1;

FIG. 3 is side view taken along line 3—3 in FIG. 1;

FIG. 4 shows a cross sectional section taken along line 4—4 in FIG. 1;

FIG. 5 shows a side view taken along line 5—5 in FIG. 1;

FIG. 6 shows a cross sectional view taken along line 6—6 in FIG. 1;

FIG. 7 shows a side view taken along line 7—7 in FIG. 1;

FIG. 11 shows the elongated element being introduced into the inserting device;

FIG. 12 shows the elongated element in its final positioning the body;

FIG. 12A shows a side view of the elongated element of FIG. 12 taken along line 12A.

FIG. 13 shows the members of the insertion device in the removal configuration;

FIG. 13A shows a side view of the member of FIG. 13 taken along line 13A;

FIG. 13B shows a cross sectional view of the members of FIG. 13 taken along line 13B; and FIG. 14 shows the insertion device being removed from the body and simultaneously separated from the elongated element;

DETAILED DESCRIPTION OF THE INVENTION

Figure 8:
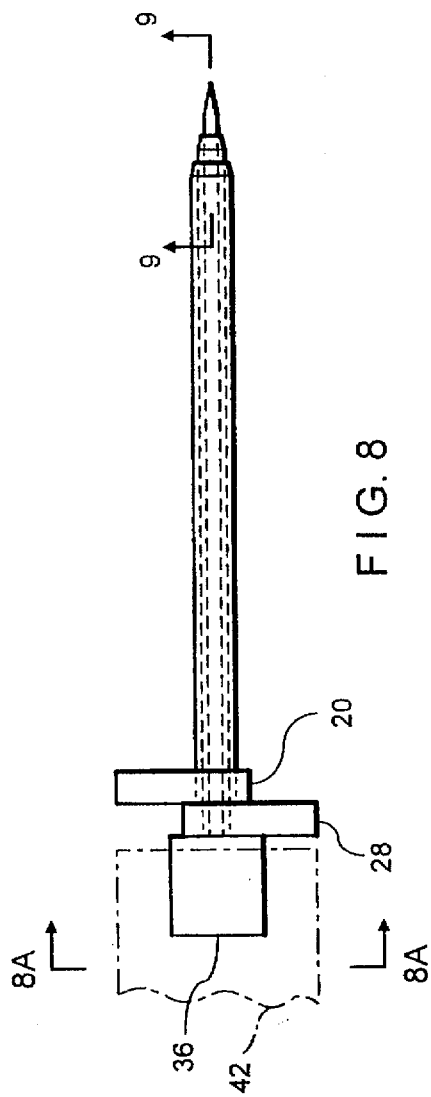
FIG. 8 shows the elements of FIG. 1 assembled to form the insertion device.

Referring now to the Figures, and more particularly to FIG. 1, an insertion device 10 constructed in accordance with this invention consists of three members: an outer member 12, an inner member 14, and, optionally, a reinforcing member 16.

Outer member 12, shown in FIGS. 1, 2 and 3, includes a tubular portion 18 and a handle 20. As seen in FIG. 2, tubular portion 20 has a substantially circular cross section with a longitudinal slit 22 formed throughout the length of portion 20. Slit 22 has a minimum width W.

Handle 20 is formed with a keyhole shaped slot 24 (FIG. 3) having an arcuate portion 24a and a straight portion 24b. The arcuate portion 24a has a radius equal to the radius of the inner wall of tubular portion 18. The straight portion 24b has a width substantially equal to W. Tubular portion 18 is attached to handle 20 so that it extends normally away from the handle 20 in a cantilevered manner. Importantly, the portion 18 is positioned and arranged so that its inner surface 18a is substantially continuous with slot portion 24a and the slit 22 is aligned with slot portion 24b.

Inner member 14, shown in FIGS. 1, 4 and 5, is similar to outer portion 12 in that it also has a tubular portion 26 and a handle 28. As seen in FIG. 4, portion 26 is also generally circular with a longitudinal slit 30 of minimum width W. Handle 28 is formed with a keyhole shaped slot 30 having a circular portion 32a having an inner radius substantially equal to the inner radius of tubular portion 26, and a straight portion 32a having width W. The portion 2b extends normally away from handle 28 with inner surface 26A being aligned with slot portion 32a and slit 30 being aligned with slot portion 32b. In addition, tubular portion 26 is dimensioned so that it fits slidingly inside tubular portion 18.

The enforcing member 16, shown in FIGS. 1, 6 and 7 is formed of an elongated solid rod or thin wire 34 and a handle 36. Rod 34 may be sharpened at one end 38. Enforcing member 16 may be for example a standard obturator, with the diameter of the rod 34 being slightly less than the diameter of inner wall 26a of tubular portion 26.

In order to use the device 10, the three members are assembled or nested together telescopically by inserting tubular portion 26 through slot portion 24a and tubular portion 18, and then inserting the rod 34 through slot portion 32a on handle 28 and then through tubular portion 26. The assembled device 10 is shown in FIGS. 8, 8A, 9 and 9A. As can be seen in these figures, the members are positioned so that the handles 20, 28 and 36 are adjacent to each other and rod 34 is surrounded by portion 26 which in turn is surrounded by portion 18. Importantly, the handles 20, 28 are aligned in a first position in which they are disposed in opposite direction along a vertical axis X—X. In this configuration, the slits 22 and 30 are disposed in opposite direction, i.e., angularly offset from each other by 180°, as shown in FIG. 9A.

Figure 9:
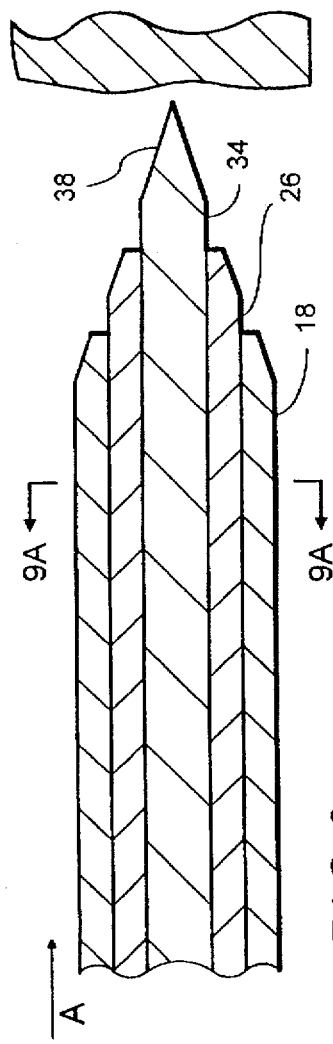
FIG. 9 shows an enlarged longitudinal partial sectional view of the device of FIG. 8 as it is introduced into the body.
Figure 8A:
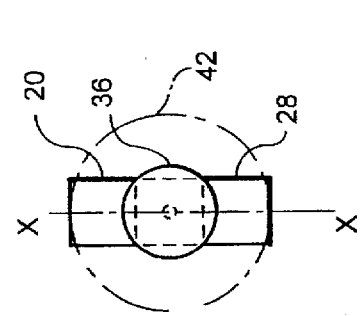
FIG. 8A shows a side view of the assembled members taken along line 8A in FIG. 8.
Figure 9A:
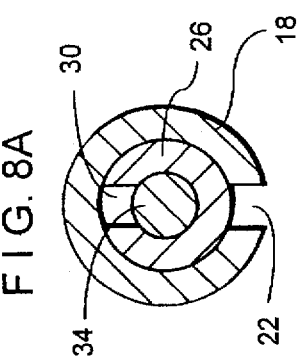
FIG. 9A shows a cross sectional view taken along line 9A—9A in FIG. 9.

As seen in FIG. 9, the lengths of portions 18, 26 and 34 are selected such that the central rod 34 extends past the tubular portion 26, which in turn extends past tubular portion 18. If possible, the portions 18, 26 may even be chamfered slightly as shown, so that the device 10 has a thickness which increases gradually from tip 38A towards the handles 20, 28, 36.

After the device 10 has been assembled, it can be introduced into the tissue 40 of patient, by advancing the device in direction A as shown in FIG. 9. Because the device 10 thickens gradually, as described above, it penetrates easily into the tissue without tearing it or causing unnecessary damage. The device 10 is advanced gradually into the tissue until tip 38 reaches a predetermined position or destination. If necessary, handle 36 of the enforcing member 16 may be engaged with a guiding element 42, shown in outline in FIG. 8, which may be, for example, a stereotactic guidance system used for guiding the device 10 through the tissue 40. During this process, the enforcing member 16 provides sufficient rigidity to device 10 to insure that the device is easily and quickly guided to the desired position within the tissue 40.

Figure 10:
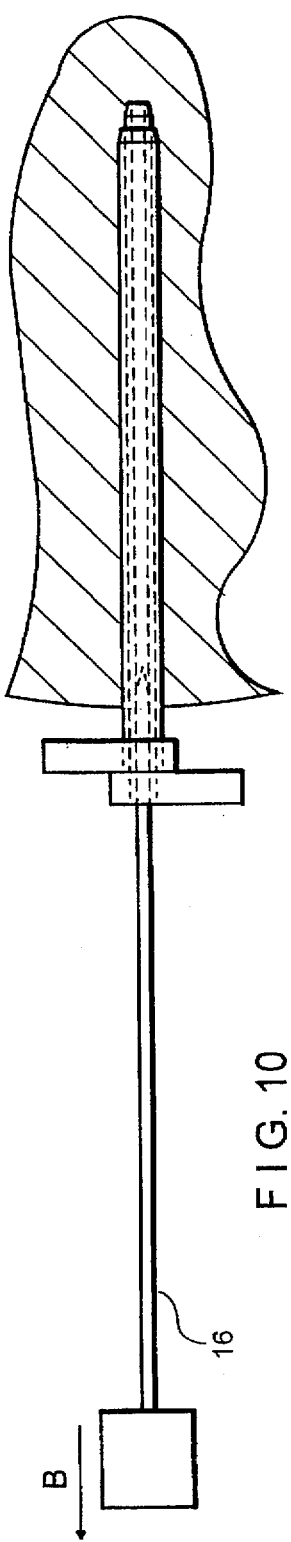
FIG. 10 shows the reinforcing member being removed.

After the device 10 has reached its desired or selected position, the enforcing member 16 is withdrawn, as illustrated in FIG. 10 by arrow B, leaving the two members 12, 14 in place. These two members define now a lumen 44 (shown in FIG. 12A) with their tubular portions 18, 26.

The whole purpose of this procedure is to install an elongated surgical element 45 into the tissue 40. This surgical element 45, shown in FIG. 11 includes a filament 46 and an enlarged portion 48.

In order to position the element 45 in tissue 40, the filament 46 is introduced into the lumen 44 and is advanced until required, as indicated in FIG. 11 by arrow C. The filament can be lubricated with a saline solution or other lubricant to make it slide easier into the lumen 44.

Next, the device 10 must be removed. In order to accomplish the removal, first the handles are positioned into a different configuration wherein they are oriented, as shown in FIG. 13, 13A and 13B so that the slot portions 24B and 32B are aligned with each other. Positioning the handles into this configuration entails rotating one of the handles, for example, inner handle 20, around the common longitudinal axis by 180°. In this second configuration, the slits 22, 30 of tubular members 18, 26 respectively are also aligned with each other as seen in FIG. 13B, to form a longitudinal opening 50 of width W from lumen 42. Dimension W is selected to be equal or slightly larger than the thickens of filament 46.

The filament 46 is normally flexible. In fact the very reason that the device 10 is needed, is that the filament 46 is too flexible to be inserted into the tissue without any insertion means. The enlarged portion 48 is now bent away from the handles 20, 28 causing the filament 46 to be withdrawn radially out of the proximal end of the lumen 44 through the opening 50, as shown in FIGS. 13 and 13A. The Two members 12, 14 can now be slipped out and removed from the tissue, as indicated in FIG. 14 by arrow D, leaving the surgical element 45 in place. The filament should be stabilized during withdrawal of the inserter in order to prevent withdrawal of the surgical element.

The dimensions of the members making up the device 10, as well as the materials used to make the same depend on the actual application, i.e., the structure and size of surgical element 45. As seen in the Figures, the diameter of rod 34 can be substantially the same as the inner diameter of surface 26a, of member 14 because the rod is slipped axially in and out of the member 14. However, the diameter of surface 26a must be somewhat larger than the diameter of filament 46 the members 12, 14 to be withdrawn with the filament 46 passing through the opening 50.

The device described above may be used, for example, to stereotactically insert an electrode array into the auditory cortex or inferior colliculus to provide auditory stimulation. An electrode array with geometry similar to a cochlear implant electrode may be used for this purpose. This type of electrode is typically 1.9" long and 0.025" in diameter. A device for this purpose can include an inner member 14 made of an 18 gauge stainless steel hypodermic needle formed with the slit 30 as described above. The outer member can be a stainless steel 118 sleeve also formed with a slit 22. The slits 22, 30 have a minimum width of 0.029" and can be made by machining or laser cutting. The rod 34 can be a 0.031" diameter stainless steel obturator wire. The handles 20, 28, 36 can be made of stainless steel or sterilizable plastic such as polysulfone. The handles are attached to the respective positions 18, 26, 34 by welding, or by using an adhesive such as epoxy. The device 10 thus constructed can be easily sterilized before and after each use with a steam autoclave or ethylene oxide gas.

The device described above has a number of advantages over the prior art. The device can be made to be sufficiently rigid to allow deep insertion, for example, up to 6", without bending, thereby insuring that the flexible surgical element is placed very accurately.

The surgical element can be a standard off-the shelf item with no modifications such as loops, hooks or other mechanical couplings required in the prior art for attachment to a insertion device. This makes the surgical element smaller, more reliable, less expensive and easier to fabricate.

The outer diameter of the insertion device need be only slightly larger than the diameter of the surgical element. For the specific embodiment set forth above the outer diameter of device 10 is only four hypodermic needle wall thicknesses, or 0.018" larger. Therefore the device makes a hole, only slightly larger than the surgical element, thereby reducing trauma to the patient.

The device can be withdrawn without causing the inserted surgical element to move from its place.

The tip of the device can be structured to conform to various profiles by changing the shape of tip 34A and the reactive lengths of the tubular portions 18, 26. Therefore, the device 10 can be tailored for various tissues of the body.

The portions of the device which are inserted into the body are smooth and have a constant cross-sectional dimensions so that the device can be easily withdrawn without causing any section thereof to break off and remain lodged in the body.

The device can be made easily and inexpensively, especially if it is made to be disposable, thereby reducing the overall cost of the whole surgical procedure.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

I claim:

1. A device for inserting a surgical instrument into a patient's body, said instrument including an elongated element, said elongated element having a preselected cross sectional dimension, said device comprising:

an outer member;

an inner member constructed and arranged to fit telescopically in said outer member;, said inner and outer members having corresponding longitudinal slits of predetermined widths at least equal to said predetermined cross-sectional dimension; and positioning members for positioning said inner and said other members selectively in a first position in which said inner and outer members define a closed longitudinal lumen for said element, and a second position in which said inner and outer members are aligned radially with said slits defining an opening for said longitudinal lumen, said opening having a dimension substantially equal to said predetermined cross sectional dimension thereby allowing the inner and outer members to be removed from said body after said element has been inserted into said body by withdrawing said inner and outer members, with said element passing through said opening.

2. The device of claim 1 wherein said inner and outer members are substantially coextensive.

3. The device of claim 1 wherein said opening extends longitudinally along said inner and outer members.

4. The device of claim 1 further including an enforcing member extending into said lumen.

5. The device of claim 4 wherein said enforcing member is removable.

6. A device for inserting an elongated surgical member into body tissues, said elongated surgical member having a preselected cross sectional dimension, said device comprising:

a first member having a first member handle and a first member tubular portion attached to said first member handle, said first member tubular portion having a permanent longitudinal slit of a first width approximately equal to said preselected cross sectional dimension; and a second member having a second member handle and a second member tubular portion attached to said second member handle, said second member tubular portion having a permanent longitudinal slit having a second width approximately equal to said preselected cross sectional dimension;

said first member being constructed and arranged to telescopically receive said second member;

said first and second members cooperating in a first position to form a lumen for receiving said elongated surgical member;

said first and second members cooperating in a second position to define an opening for said lumen for allowing said members to separate from said surgical member once said surgical member is placed in said lumen, with said first and second members being disposed in said second position with said slits being aligned to define said opening.

7. The device of claim 6 wherein in said first position, said members are oriented with said slits being angularly offset from each other.

8. The device of claim 6 wherein said slits have a minimum width substantially equal to the cross sectional dimension of said surgical member.

9. The device of claim 6 further composing an enforcing element arranged and constructed to fit into said lumen to enforce said first and second members while said first and second members are inserted into said lumen.

10. The device of claim 9 wherein said enforcing element includes an elongated rod having a diameter substantially equal to an inner diameter of said second member.

11. The device of claim 9 wherein said enforcing element includes an enforcing element handle.

12. A method of inserting an elongated surgical element having a preselected cross sectional dimension into a body tissue, said method comprising the steps of:

provinding an inserting device, said device including two members, each having a longitudinal slit with a width substantially equal to said preselected dimension, said members cooperating to form in one position an elongated tubular lumen and cooperating in a second position to define an opening in a second position;

introducing said inserting device into said tissue with said lumen extending toward a preselected position in said tissues;

introducing said elongated member into said lumen;

moving said members with respect to each other to said second position in which said members form said opening in said lumen; and removing said inserting device from said tissues with said surgical member passing through said opening to leave said surgical member inserted in said tissues.

13. The method of claim 12 further comprising the step of inserting an enforcing element into said lumen prior to the introduction of said inserting device into said body.

14. The method of claim 13 further comprising the step of withdrawing said enforcing element from said lumen prior to the introduction of said surgical member into said lumen.

15. The device of claim 6 wherein said first and second members are made of stainless steel.

16. The device of claim 6 wherein said first and second members are made of a stiff material.

* * * * *